United States Patent
Fukuda et al.

(10) Patent No.: US 7,214,667 B2
(45) Date of Patent: May 8, 2007

(54) DRUGS AGAINST ARTICULAR FAILURE

(75) Inventors: Shigeharu Fukuda, Okayama (JP); Takeshi Ario, Okayama (JP); Toshio Miyake, Okayama (JP)

(73) Assignee: Kabushiki Kaisha Hayashibara Seibutsu Kagaku Kenyujo, Okayama (JP)

( * ) Notice: Subject to any disclaimer, the term of this patent is extended or adjusted under 35 U.S.C. 154(b) by 2 days.

(21) Appl. No.: 11/136,717

(22) Filed: May 25, 2005

(65) Prior Publication Data

US 2005/0277617 A1 Dec. 15, 2005

Related U.S. Application Data

(63) Continuation-in-part of application No. 10/451,224, filed on Jun. 23, 2003, now abandoned.

(30) Foreign Application Priority Data

Dec. 22, 2000 (JP) ............... 2000-391390

(51) Int. Cl.
*A01N 43/04* (2006.01)
*A61K 31/70* (2006.01)
*C07H 5/04* (2006.01)
*C07H 5/06* (2006.01)

(52) U.S. Cl. ............... 514/62; 536/21; 536/55.2; 536/123.13; 514/53; 514/56

(58) Field of Classification Search .............. 536/21, 536/55.2, 123.13; 514/53, 56, 62
See application file for complete search history.

(56) References Cited

U.S. PATENT DOCUMENTS

| 5,229,374 A | 7/1993 | Burton et al. |
| 5,587,363 A | 12/1996 | Henderson |
| 5,892,026 A | 4/1999 | Okada et al. |
| 5,916,565 A | 6/1999 | Rose et al. |
| 5,935,636 A | 8/1999 | Nishimoto et al. |
| 5,981,498 A | 11/1999 | Fukuda et al. |
| 6,162,787 A | 12/2000 | Sorgente et al. |

FOREIGN PATENT DOCUMENTS

| EP | 0606753 A2 | 7/1994 |
| EP | 0628630 A2 | 12/1994 |
| EP | 0636693 A2 | 2/1995 |
| EP | 0671470 A2 | 9/1995 |
| EP | 0674005 A2 | 9/1995 |
| EP | 0688866 A1 | 12/1995 |
| EP | 0688867 A2 | 12/1995 |
| EP | 0695804 A2 | 2/1996 |
| EP | 0697461 A1 | 2/1996 |
| EP | 0704531 A2 | 4/1996 |
| EP | 0709461 A1 | 5/1996 |
| EP | 0938899 A2 | 9/1999 |
| EP | 0955050 A1 | 11/1999 |
| JP | 07-143876 A | 6/1995 |
| JP | 07-170977 A | 7/1995 |
| JP | 07-213283 A | 8/1995 |
| JP | 07-298880 A | 11/1995 |
| JP | 07-322883 A | 12/1995 |
| JP | 08-000263 A | 1/1996 |
| JP | 08-066187 A | 3/1996 |
| JP | 08-66188 A | 3/1996 |
| JP | 08-084586 A | 4/1996 |
| JP | 08-149980 A | 6/1996 |
| JP | 08-336388 A | 12/1996 |
| JP | 2971579 B2 | 8/1999 |
| JP | 2000-198736 A | 7/2000 |
| JP | 2001-072582 A | 3/2001 |
| JP | 2001-302496 A | 10/2001 |
| WO | WO-93/09766 A1 | 5/1993 |
| WO | WO-94/22453 1 | 10/1994 |
| WO | WO-98/25631 A | 6/1998 |

OTHER PUBLICATIONS

D.T. Walz et al "Adjuvant-Induced Arthritis in Rats. II. Drug Effects on Physiologic, Biochemical and Immunologic Parameters", Journal of Pharmacology and Experimental Therapy, vol. 178 (1971), pp. 233-231.

G.H. Christie "An Electro-Mechanical Method for Measuring Delayed Hypersensitivity in Mice by Increase of Ear Thickness" Journal of Immunological Methods vol. 8, (1975) pp. 257-262.

Kuniaki Terato et al, "Histological Immunological and Biochemical Studies on Type II Collagen-Induced Arthritis in Rats" Biomedical Research, vol. 3, (1982) pp. 495-505.

Fagan, "General Information on Arthritis", Discoveryhealth.com (2005).

Webster's II: New Riverside University Dictionary (1994), p. 933.

*Primary Examiner*—Patrick Lewis
(74) *Attorney, Agent, or Firm*—Browdy & Neimark, PLLC

(57) ABSTRACT

The object of the present invention is to provide a composition which exerts a higher effect on recovering health from articular disorders than that attained by amino sugars and glycosaminoglycans. The present invention solves the object by providing an agent for treating articular disorders, comprising an amino sugar and trehalose as effective ingredients.

14 Claims, No Drawings

DRUGS AGAINST ARTICULAR FAILURE

CROSS-REFERENCE TO RELATED APPLICATION

This application is a continuation-in-part application of application Ser. No. 10/451,224, filed Jun. 23, 2003, abandoned in favor of the present application.

TECHNICAL FIELD

The present invention relates to a novel agent for treating articular disorders, more particularly, to the agent which comprises an amino sugar and trehalose as effective ingredients.

BACKGROUND ART

Articulations in mammals including humans are mechanically stimulated during their physical activities and exposed to risks such as inflammation and physical destruction. Examples of factors of causing disorders in articulations (hereinafter, briefly called "articular disorders") are infections, injuries, allergies, metabolic disorders, corpulences, and blood circulation disorders. It has been pointed out that the crisis rate of articular disorders increases as aging, and articular disorders are becoming to be a social problem in this aging society.

As articular disorders generally accompany inflammations, they are treated with anti-inflammatories in many cases. However, treatments thereof can be only effective for temporarily suppressing some symptoms accompanied by articular disorders such as pains and swellings. There is nothing but the action of recovery by living bodies to intrinsically cure the disorders.

The specification of Japanese Patent No. 2,971,579 discloses a composition comprising an effective amount of an amino sugar or a salt thereof, and a glycosaminoglycan or a salt thereof for treating damaged connective tissues and arthritis or for keeping treated conditions. The composition promotes the recovery action of living bodies on damaged connective tissues through the functions of amino sugars and glycosaminoglycans. It may be as a proposal to solve the problem of current treatments with anti-inflammatories. However, the establishment of more effective agents for treating articular disorders, which use the above functions of amino sugars and glycosaminoglycans, has been desired to solve the problem of articular disorders becoming to be a social problem. In addition, these amino sugars and glycosaminoglycans may give some people a strange taste and flavor when taken orally, and therefore, it has been greatly expected that agents for treating articular disorders should be improved in their taste and flavor although it contains amino sugars and glycosaminoglycans.

DISCLOSURE OF INVENTION

In view of the above backgrounds, the object of the present invention is to provide an agent for treating articular disorders, which exerts an effect of recovery action on articular disorders at a level exceeding the effect of amino sugars and glycosaminoglycans alone and has a satisfactory taste and flavor when taken orally.

The present inventors widely screened a variety of saccharides, which had been reported as useful and functional materials for foods, cosmetics, pharmaceuticals, etc., by using a model system with experimental animals to judge whether they enhance or not the recovery promoting action of amino sugars and glycosaminoglycans on articular disorders. As a result, it was revealed that trehalose, a non-reducing disaccharide composed of glucoses, has an activity of enhancing the action of amino sugars. It was also confirmed that, in the case of administering amino sugars to improve articular disorders, the administration of trehalose in combination with the amino sugars reduces the amount of amino sugars and imparts a satisfactory taste and flavor when taken orally. Thus, the present invention was made based on the self-finding of the present inventors.

The present invention solves the above object by providing an agent for treating articular disorders, which comprises an amino sugar and trehalose as effective ingredients.

BEST MODE FOR CARRYING OUT THE INVENTION

The present invention relates to an agent for treating articular disorders, which comprises an amino sugar and trehalose as effective ingredients. The agent of the present invention has activities of preventing, improving, alleviating, and curing disorders or diseases of articulations of living bodies such as mammals including humans (hereinafter, may be simply called "activities of treating articular disorders"). The agent of the present invention is characterized by the fact that it exerts the above activities of treating articular disorders at a remarkably enhanced level than in the sole use of amino sugars. The character can be confirmed by animal experiments described in detail in the later-described experiments.

The term "amino sugars as referred to as in the present invention means a compound(s) having a structure where hydroxyl group in saccharides are substituted with amino groups, or its derivative or salt. The amino sugars used in the present invention are not restricted to specific ones in terms of their chemical structures, purities, properties, and production methods, as long as they effectively solve the object of the present invention when applied to mammals including humans in a composition form combined with trehalose as described later. The amino sugars, which are relatively preferably used in practicing the present invention, are those which exist in nature in a free form or as components of polysaccharides, glycoproteins, and glycolipids, etc; as well as glucosamine, mannosamine, neuraminic acid, galactosamine, and their derivatives. Examples of these derivatives, confirmed their existence in nature, are acylated derivatives such as N-acetylated derivatives, sulfated derivatives such as N-sulfated derivatives and O-sulfated derivatives, and glycolylated derivatives such as N-glycolylated derivatives of amino sugars. Among the above amino sugars and derivatives thereof, glucosamine, N-acetylglucosamine, mannosamine, and N-acetylmannosamine have inherently a relatively-high activity of treating articular disorders and are advantageously used in practicing the present invention. The amino sugars used in the present invention can be prepared by collecting polysaccharides, glycoproteins, etc., having the amino sugars as components from mammals, fishes, mollusks, arthropods, fungi, bacteria etc., by conventional methods; hydrolyzing them under acidic conditions or with appropriate enzymes; subjecting the resultant mixtures to conventional methods for separating and purifying saccharides such as chromatography. Commercially available preparations of amino sugars for foods, cosmetics, etc., for example, "NATURAL GLUCOSAMINE™", a product name of glucosamine, and "MARINE SWEET™", a product name of N-acetylglucosamine, both of which are commercialized by Yaizu Suisankagaku Industry Co., Ltd., Shizuoka, Japan, can be arbitrarily used.

The term "trehalose" as referred to as in the present invention means a disaccharide which two molecules of glucose are linked together at their reducing groups in the $\alpha,\alpha$-linkage. Trehalose used in the present invention is not restricted to its specific purity, property, and preparation method as long as trehalose compositions with amino sugars can exert an effect to solve the object of the present invention, when used in a composition form with amino sugars and applied to humans by the methods described below.

Trehalose can be prepared by different methods: For example, with an economical view point, methods where a non-reducing saccharide-forming enzyme and a trehalose-releasing enzyme are allowed to act on partial starch hydrolyzates, as disclosed in Japanese Patent Kokai Nos. 143,876/95, 213,283/95, 322,883/95, 298,880/95, 66,187/96, 66,188/96, 336,388/96, and 84,586/96 can be preferably used. According to the above methods, trehalose can be obtained in a higher yield from starches, a low-cost material. Examples of commercialized products prepared by the above methods are "TREHA®", a crystalline hydrous trehalose and "TREHASTAR®", a trehalose syrup, which are commercialized by Hayashibara Shoji Inc., Okayama, Japan. Trehalose can be prepared by subjecting maltose to the action, for example, of a maltose/trehalose converting enzyme as disclosed in any one of Japanese Patent Kokai Nos. 170,977/95, 263/96, and 149,980/96 or a conventional maltose phosphorylase and a trehalose phosphorylase in combination. Further, anhydrous trehalose can be prepared, for example, by drying the above crystalline hydrous trehalose at a temperature of 70 to 160° C. under a normal or reduced pressure, preferably, at a temperature of 80 to 100° C. under a reduced pressure; or placing in a crystallizer a relatively-high trehalose content solution with a moisture content of less than 10%, stirring the solution in the presence of a seed crystal at a temperature of 50 to 160° C., preferably, 80 to 140° C., to prepare a massecuite containing crystalline anhydrous trehalose, crystallizing trehalose from the massecuite, and pulverizing the resulting crystals by a method of block pulverization, fluidied-bed granulation, spray drying, etc., under a relatively-high temperature and a drying condition. Trehalose obtained by the above methods can be advantageously used in the present invention.

The proportion of trehalose and an amino sugar(s) in the agent for treating articular disorders of the present invention is not restricted to a specific ratio as long as the agent exerts an effect of solving the object of the present invention. For example, from a view point of remarkably enhancing the activity of amino sugars for treating articular disorders by adding trehalose thereto, it is preferable to use trehalose in a weight ratio of at least one quarter to the amino sugar(s) on a dry solid basis (d.s.b.). The term "d.s.b." as referred to as in the present invention means the weight of a material after evaporating water, contained as the free and bound water, from the material. Some amino sugars may give some people a somewhat strange flavor and taste, or even an undesirable taste when taken orally. As trehalose can improve such a strange flavor and taste and an undesirable taste, the agent for treating articular disorders should more preferably contain trehalose as much as possible when used orally. In order to obtain a satisfactory flavor and taste and to exert remarkable activity for treating articular disorders with an amount as low as possible, the agent for treating articular disorders should preferably contain trehalose, usually, in a weight ratio of at most 50-folds, desirably, 20-folds to an amino sugar(s), d.s.b. Amino sugars in general have the defect in their expensiveness in comparison with other food materials such as saccharides for personal daily use. In the agent for treating articular disorders of the present invention, the activity for treating articular disorders inherent to amino sugars will be enhanced, the amount of amino sugars to obtain the desired effect is more reduced than in the sole use of amino sugars. Therefore, the agent for treating articular disorders of the present invention has the advantage that it exerts the desired activity and is provided at a lower cost than a composition comprising an amino sugar(s) without trehalose.

Further the addition of glycosaminoglycans to the agent may more remarkably enhance the activity of the agent of the present invention, depending on the objective diseases or symptoms. The term "glycosaminoglycans" as referred to as in the present invention means acid polysaccharides containing amino sugars as a structure unit, and their salts, independently of the chemical structures of other structure units other than amino sugars, and the molecular weight and purity of glycosaminoglycans. The glycosaminoglycans, which are relatively preferably used in practicing the present invention, are those which are found in nature or their partial hydrolyzates: Chondroitin sulfates such as chondroitin 4-sulfate; chondroitin; keratan sulfate; hyaluronic acid; dermatan sulfate; heparin; and heparan sulfate. The glycosaminoglycans used in the present invention can be prepared from mammalians, fishes, mollusks, arthropods, fungi, bacteria, etc., by conventional purification methods for acidic polysaccharides. Commercially available preparations of glycosaminoglycans for foods, cosmetics, etc., for example, "MUCOTEIN-DK™", chondroitin sulfate is a food grade, commercialized by Yaizu Suisankagaku Industry Co., Ltd., Shizuoka, Japan, can be arbitrarily used.

Since amino sugars, having unmodified amino groups, have a relatively high reactivity, they are susceptible to deteriorate such as coloration. Therefore, the agent for treating articular disorders may result in a problem of lacking preservation stability depending on the kinds of amino sugars used. Such a problem can be solved by using salts of the amino sugars which are formed by reacting with acid substances. When the agent for treating articular disorders is in the form of a liquid, the above problem can be solved by adding acid substances to the agent. The acid substances used in the present invention include any physiologically acceptable substances which are generally used in the fields such as food, cosmetic and pharmaceutical fields where the agent is applicable to; inorganic acids such as hydrochloric acid, sulfuric acid, carbonic acid, and phosphoric acid; and organic acids such as acetic acid, adipic acid, citric acid, gluconic acid, tartaric acid, lactic acid, fumaric acid, malic acid, L-ascorbic acid, and glycosyl L-ascorbic acid. Among these acid materials, glycosyl L-ascorbic acids such as 2-o-α-D-glucopyranosyl L-ascorbic acid ("AA2G™", a food or cosmetic grade glycosyl L-ascorbic acid commercialized by Hayashibara Shoji Inc., Okayama, Japan) and acylated derivatives of glycosyl L-ascorbic acid have an improved stability in comparison with L-ascorbic acid and exert functions as vitamin C in living bodies. Therefore, the addition of L-ascorbic acid to the agent of the present invention is particularly useful in practicing the present invention, as they stabilize and impart the functions of vitamin C to the agent.

If necessary, the following other ingredients can be also advantageously incorporated into the agent for treating articular disorders of the present invention; emulsifiers, fillers, pH-controlling agents, sweeteners, flavors, spices, colorings, vitamins, amino acids, etc. These ingredients can be freely used as long as they do not affect the desired actions of the agent. Any ingredients used as additives in the fields of conventional agents for treating articular disorders, particularly, in the fields of foods, cosmetics, pharmaceuticals, etc., can be arbitrarily used in the present invention.

The agent for treating articular disorders of the present invention comprising the above ingredients is not specially restricted to a specific form and can be provided in any forms of solids, semisolids, liquids, and mixtures thereof such as powders, granules, tablets, gels, pastes, milky lotions, and solutions. The amount of amino sugars preferably incorporated into the agent of the present invention is usually 0.01 to 80%, desirably, 0.05 to 60%, and more desirably, 0.1 to 40%, d.s.b.

Examples of symptoms or diseases, where the agent of the present invention can exert the activity of treating articular disorders, include arthritis caused by infections, injuries, allergies, metabolic disorders, etc., rheumatoids such as chronic rheumatoid arthritis, and systemic lupus erythematosus; articular disorders accompanied by gout, arthropathy such as osteoarthritis, internal derangement, hydrarthrosis, stiff neck, lumbago, etc. Varying the effects depending on the use of the agent or the types of diseases to be treated, the agent can exert desired prophylactic and alleviative effects, or even therapeutic effects on swelling, pain, inflammation, and destroying of articulations without seriously affecting living bodies. The agent for treating articular disorder can be used to prevent the onset of articulation disorders, as well as to improve, alleviate, and cure the symptoms after their onsets. The application routes or the administration routes can be appropriately selected from an oral intake, percutaneous absorption, and other physiologically acceptable routes depending on the symptoms to be treated. Varying the effective dose of the agent for treating articular disorders of the present invention depending on its composition, application route, and symptoms of targeted diseases, the dose of the amino sugars is usually 100 mg (d.s.b.) or less, desirably, 15 mg or less, more desirably, 10 mg or less, particularly 5 mg or less, per kg body weight per day when orally taken. The lower limit of the dose is not specifically restricted as long as the desired effects are obtained depending on the administration routes, for example, it is usually 0.01 mg or more, and desirably, 0.1 mg, d.s.b., or more per kg body weight per day when taken orally. The agent for treating articular disorders comprising trehalose and an amino sugar (s) can be taken at one or two to five times a day every day or at appropriate intervals, depending on the symptoms at a dose selected form the above range.

The agent for treating articular disorders of the present invention is advantageously used as a health food, hospital diet, beverage, and skin external agent for preventing, alleviating or curing articulation disorders. Further, the agent is also useful as a coadjuvant for reinforcing pharmaceutical effects of therapeutic or prophylactic medicines for treating articular disorders. Furthermore, the agent can be also used as an ingredient to impart the activity of treating articular disorders to general foods, health foods, cosmetics, etc. The agent for treating articular disorders can be incorporated into the following foods: Frozen desserts such as an ice cream, ice candy, and sherbet; syrups such as a "korimitsu" (a sugar syrup for shaved ice); spreads and pastes such as a butter cream, custard cream, flour paste, peanut paste, and fruit paste; Western confectioneries such as a chocolate, jelly, candy, gummy jelly, caramel, chewing gum, pudding, cream puff, and sponge cake; processed fruits and vegetables such as a jam, marmalade, syrup-zuke" (a fruit pickle), and "toka" (conserves); Japanese confectioneries such as a "manju" (a bun with a bean-jam), "uiro" (a sweet rice jelly), "an" (a bean jam), "yokan" (a sweet jelly of beans), "mizu-yokan" (a soft adzuki-bean jelly), pao de Castella, and "amedama (a Japanese toffee); and seasonings such as a soy sauce, powdered soy sauce, 'miso", "funmatsu-miso" (a powdered miso), mayonnaise, dressing, vinegar, "sanbai-zu" (a sauce of sugar, soy sauce and vinegar), table sugar, and coffee sugar. The agent for treating articular disorders can be incorporated into the following beverages: Alcoholic beverages such as a synthetic sake, fermented liquor, fruit wine, and Western liquors; and soft drinks such as a juice, mineral beverage, carbonated beverage, sour milk beverage, beverage containing lactic acid bacteria, sport drink, supplemental drink, tea, black tea, oolong tea, coffee, and cocoa. The agent for treating articular disorders can be incorporated into cosmetics in the form of a lotion, solution, milky lotion, powder, cream, paste, bath agent, and pack agent. The agent for treating articular disorders can be incorporated into pharmaceuticals in the form of a powder, liquid, syrup, tablet, capsule, ointment, cataplasm, or spray. A suitable amount of the amino sugar(s) in a composition such as foods, cosmetics, and pharmaceuticals comprising either the above agent for treating articular disorders or the effective ingredient of the agent is usually 0.00001 to 20%, desirably, 0.0001 to 10%, more desirably, 0.001 to 2%, d.s.b.

The following experiments and examples explain the present invention in more detail.

Experiment

Alleviation Effect of Amino Sugar or Glycosaminoglycan on Arthritis Induced Rat, and the Effect of Trehalose on its Alleviation Effect Experiment 1

Effect of glucosamine, N-acetylglucosamine chondroitin 4-sulfate, and trehalose

Thirty-six female Lewis rats, aged 6-weeks, were divided into 12 groups consisting of three rats per group. Glucosamine, N-acetylglucosamine, chondroitin 4-sulfate, and crystalline hydrous trehalose, which were all in a reagent grade, and designated as "test compounds" hereinafter), were respectively dissolved in phosphate buffer saline (described as "PBS" hereinafter), and intraperitoneally injected alone or in an appropriate combination daily to the rats of the group Nos. 1 to 11 at the doses in the following Table 2. As a control, PBS was administered daily to each rat of the group No. 12 at a dose of 1 ml per day by the same administration route as above. Hereinafter, the day number means a day counted from the starting day of administration. In accordance with the method of inducing arthritis by type II collagen immunization described by K. Terato, in "*Biomedical research*", Vol. 3, pp. 495–505, 1982, on day 3, 800 µg/head of a type II collagen from bovine in a reagent grade along with Freund's incomplete adjuvant was administered to the dorsal subcutaneous; and on day 10, a fresh preparation of the same collagen and adjuvant as used above were administered at a dose of about ¹⁄₁₀ of that of on day 3. Test compounds were administered to the rats daily until day 24.

During the term of the above experiment, on day 3 just before the administration of collagen and on day 24 just after the administration of the test compounds, both hind foot volumes of every rat were measured according to the method described by D. T. Walz in "*Journal of Experimental Therapy*", Vol. 152, pp. 116–121, 1971. Increasing rate (%)

of the total hind foot volume of each rat was calculated by substituting the data for the Formula 1 below.

Increasing rate of hind foot volume (%)=[{(Measured volume on day 24)−(Measured volume on day 3)}/(Measured volume on day 3)]×100     Formula 1

This experiment confirmed that the hind foot volume of the rats of the control group remarkable increased (some were over 120%) due to the onset of edema induced by arthritis. As not shown in the above, in the case of administering indomethacin, an anti-inflammatory, at a dose of 3 mg/kg body weight to each rat, induced arthritis by the above method, their hind foot volumes slightly increased (some were under an increasing percentage of 20%). From the above results, it was confirmed that this experiment is a reliable system to evaluate the effect of compounds or compositions for treating, preventing, or alleviating arthritis.

The effect of alleviating arthritis for each test compound was judged on the basis of the criterion described in the following Table 1, after calculating the averages of increased rates of hind foot volumes in the rats of the group Nos. 1 to 11 and the relative values of the above averages when the average in the control group was regarded as 100. The results are in Table 2

TABLE 1

| Relative value of the average of increasing rate of hind foot volume when the average in the control group was regarded as 100 | Judgment of the effect of alleviating arthritis | Symbol |
| --- | --- | --- |
| 67 or more | Low or none | − |
| 33 or more but less than 67 | High | + |
| Less than 33 | Higher | ++ |

TABLE 2

| Group No. | Dose of test compound* (mg/kg body weight/day) | | | | Relative value | Judgment (symbol) |
| --- | --- | --- | --- | --- | --- | --- |
| | GlcN | GlcNAc | Ch4S | Trehalose | | |
| 1 | 100 | — | — | — | 88 | − |
| 2 | — | 100 | — | — | 89 | − |
| 3 | — | — | 50 | — | 95 | − |
| 4 | 100 | — | 50 | — | 82 | − |
| 5 | — | 100 | 50 | — | 85 | − |
| 6 | — | — | — | 200 | 98 | − |
| 7 | 100 | — | — | 200 | 42 | + |
| 8 | — | 100 | — | 200 | 45 | + |
| 9 | — | — | 50 | 200 | 87 | − |
| 10 | 100 | — | 50 | 200 | 15 | ++ |
| 11 | — | 100 | 50 | 200 | 19 | ++ |
| 12** | — | — | — | — | 100 | Control |

*GlcN and GlcNAc and Ch4S mean glucosamine, and N-acetylglucosamine, and chondroitin 4-sulfate respectively. Doses (mg) are shown based on the dry solid basis.
**PBS was administered in an amount of 1 ml/day/head as a control.

The increasing rates of the hind foot volumes of the rats in the group Nos. 1 to 5 administered with glucosamine, N-acetylglucosamine, or chondroitin 4-sulfate alone or in a combination were lower than that of the control group, while those in the group Nos. 4 and 5 administered with the test compounds in combination were particularly low. However, as shown in the results of the group Nos. 1 to 5 in Table 2, the alleviation effects of these groups were judged as low or none (symbol "−") when evaluated based on the criterion described in Table 1. No difference was found in increasing rate of hind foot volume between the group No. 6 administered with trehalose alone and the control group.

As shown in the results of the group Nos. 7 and 8 in Table 2, the effect of alleviating arthritis administered with trehalose and glucosamine or N-acetylglucosamine in combination was judged as high (symbol "+"). As shown in the result of the group No. 9, the effect exerted by the combination administration of chondroitin sulfate and trehalose was judged as low or none (symbol "−") similarly as in the group Nos. 3 to 5 with chondroitin sulfate alone without trehalose. The above results indicate that glucosamine, N-acetylglucosamine, and chondroitin 4-sulfate inherently have the effect of alleviating arthritis, and trehalose remarkably enhances the inherent effect of glucosamine and N-acetylglucosamine.

As found in the results of the group Nos. 10 and 11 in Table 2, the effect of alleviating arthritis exerted by the administration of glucosamine or N-acetylglucosamine, or the combination administration of trehalose and chondroitin 4-sulfate marked a higher level (symbol "++") than those of the group Nos. 7 and 8. Judging from the overall results of the above experiments, the effect of trehalose for enhancing the effect of alleviating arthritis exerted by glucosamine and N-acetylglucosamine, is more enhanced when used with chondroitin 4-sulfate.

Another animal experiment similar to those for the rats in the group Nos. 7 to 12 was conducted by a modified administration schedule of test compounds. Rats were administered with test compounds daily from day 17 (the day when the increase of hind foot volume was firstly observed) to day 31, resulting in a tendency similar to the above experiments. Further, other animal experiment similar to those for the rats in the group Nos. 7 to 12 except for replacing an intraperitoneally injection with an oral administration using a sonde (stomach tube) was conducted, resulting in a tendency similarly to the above experiments. The above results confirm that the phenomenon that the effect of alleviating arthritis by amino sugars is enhanced by the combination use of trehalose is observed independently of administration schedule and route.

Experiment 2

Effective Dose of Glucosamine to Alleviate Arthritis when Used with Trehalose

Rats, induced arthritis by type II collagen immunization, were experimented similarly as in Experiment 1 in such a manner of administering trehalose daily in an amount of 200 mg/kg body weight/day in accordance with the treatment for the group No. 7 or 8 in Experiment 1, and glucosamine or N-acetylglucosamine at a successively reduced dose. As a result, the effect of glucosamine or N-acetylglucosamine with trehalose was judged as high (symbol "+") even with the tested minimum amount of 5 mg/kg body weight/day. Considering the result of Experiment 1 judged as low or none of the alleviation effect (group Nos. 1 and 2, symbol "−"), when the rats were administered with 100 mg/kg body weight/day of glucosamine or N-acetylglucosamine alone, the combination use of trehalose greatly reduced the amount of glucosamine or N-acetylglucosamine required to alleviate arthritis.

Experiment 3

Effects of mannosamine, N-acetylmannosamine, keratan sulfate, and Various saccharides An animal experiment using rats similarly as in Experiment 1 was carried out by using mannosamine and N-acetylmannosamine instead of glucosamine and N-acetylglucosamine, and keratan sulfate instead of chondroitin 4-sulfate, resulting in a similar result as in Experiment 1.

The result indicates that trehalose enhances the alleviation effect of amino sugars on arthritis, and the effect of trehalose is more enhanced when used with a glycosaminoglycan. In accordance with Experiment 1, another animal experiment using glucose, maltose, sorbitol, maltitol, or neotrehalose instead of trehalose was carried out. There was found no enhanced effect by the saccharides other than trehalose on the alleviation effect of amino sugars on arthritis as found in trehalose. The result indicates that the enhancement of the alleviation effect of amino sugars on arthritis is not exerted by saccharides in general but specific to trehalose.

Experiment 4

Proportion of Trehalose to Enhance the Effect of Alleviating Arthritis by Amino Sugars Twenty-seven female Lewis rats, aged 6-weeks, were divided into nine groups consisting of three rats per group. After dissolving in PBS, glucosamine, N-acetylglucosamine, and crystalline hydrous trehalose, which were all in a reagent grade, were intraperitoneally injected alone or in an appropriate combination daily to the rats of the group Nos. 1 to 8 at the doses in Table 3 below. As a control, 1 ml per day of PBS was administered daily to each rat of the group No. 9 by the same administration route. The time scale was expressed with a day counted from day 0 for the starting day of administration. After all the rats were induced arthritis with type II collagen immunization under the same schedule and dose as in Experiment 1, the test compounds were administered daily until day 24. On days 3 and 24, the both hind foot volumes of each rat were measured and judged to evaluate the effect of alleviating arthritis in each group administered with each test compound similarly as the method in Experiment 1. These results are tabulated in Table 3.

TABLE 3

| Group No. | Dose of test compound* (mg/kg body weight/day) | | | Relative value | Judgment (Symbol) |
| --- | --- | --- | --- | --- | --- |
| | GlcN | GlcNAc | Trehalose | | |
| 1 | 100 | — | 400 | 39 | + |
| 2 | 100 | — | 100 | 43 | + |
| 3 | 100 | — | 25 | 57 | + |
| 4 | 100 | — | 6.25 | 82 | − |
| 5 | — | 100 | 400 | 35 | + |
| 6 | — | 100 | 100 | 37 | + |
| 7 | — | 100 | 25 | 52 | + |
| 8 | — | 100 | 6.25 | 80 | − |
| 9** | — | — | — | 100 | Control |

*GlcN and GlcNAc mean glucosamine and N-acetylglucosamine respectively.
Doses (mg) are shown based on the dry solid basis.
**PBS was administered in an amount of 1 ml/day/head as a control.

As shown in Table 3, a strong effect on alleviating arthritis was observed when trehalose was used in a weight ratio of at least one quarter to glucosamine or N-acetylglucosamine, d.s.b., (group Nos. 1 to 3, group Nos.). 5 to 7). When trehalose was used in a weight ratio of 1/16 to any of the amino sugars (group Nos. 4 and 8), the increasing rates of both hind foot volumes of the rats were lower than that of the control group and judged as low or none in terms of the judgement of the effect of alleviation. In the case of another animal experiment using mannosamine or N-acetylmannosamine instead of glucosamine or N-acetylglucosamine, a similar result was observed as in this experiment.

Experiment for Reference

Effect of Amino Sugars, Glycosaminoglycans and Trehalose on Edema Induced Rat's Earlap After measuring the earlap thickness of male ICR mice, aged 4-weeks, according to the method described by G. H. Christie, "*Journal of Immunological Methods*", Vol. 8, pp. 257–262, 1975, 0.4 µg of 12-O-tetradecanoilphorbol13-acetate (hereinafter, abbreviated as "TPA"), dissolved in acetone, was applied in a usual manner over each of the inner and outer surfaces of the mice earlaps on the parts to be measured. Thirty-six mice with TPA were divided into 12 groups consisting of three rats per group. After dissolving in a 0.5% aqueous traganth gum solution glucosamine, N-acetylglucosamine, chondroitin 4-sulfate, or trehalose, which were all in a reagent grade, the resulting solutions were orally administered alone or in an appropriate combination to the mice of the group Nos. 1 to 11 at the daily doses in Table 2 in Experiment 1 by using as a solvent a 0.5% (w/v) aqueous traganth gum solution. As a control, 0.2 ml of a 0.5% (w/v) aqueous traganth gum solution was orally administrated to the mice of the group 12 through a sonde (stomach tube). Six hours after the TPA application, the mice were measured for earlap thickness similarly as the measurement before the TPA application. Swelling rates of earlap thickness of rats in each group were calculated based on the data of the earlap thickness between the earlap thickness of just before and six hours after the TPA application in each mouse, and averaged for an index of the degree of generating auricular edema.

It was confirmed that the swelling rate of earlap in the control group was about 200%, and the TPA application induced edema. While, in the mice administered with glucosamine, N-acetylglucosamine, chondroitin 4-sulfate, and trehalose in an appropriate combination, there was found no enhancement of the effect of alleviating edema by glucosamine or N-acetylglucosamine exerted by the combination use of trehalose as found in Experiment 1. Considering the results of this Experiment for Reference and Experiments 1 to 4, the enhancement of alleviation effect on arthritis by amino sugars found in Experiments 1 to 4 would not be commonly found in inflammatory diseases. Therefore, it is concluded that the effects of the combination use of amino acids and trehalose, observed in Experiments 1 to 4, correspond to the alleviation of edema in articulations through recovery from articular disorders or diseases.

EXAMPLE 1

Agent for Treating Articular Disorders

Four parts by weight of crystalline hydrous trehalose ("TREHA®", commercialized by Hayashibara Shoji Inc., Okayama, Japan) and one part by weight of glucosamine ("NATURAL GLUCOSAMINE™", commercialized by Yaizu Suisankagaku Industry Co. Ltd., Shizuoka, Japan) were mixed well to obtain the captioned product in the form of a powder.

Since the product remarkably exerts an action for treating articular disorders and has a mild sweetness, it is useful as a health food to prevent or alleviate articular disorder such as arthritis and rheumatoid. The product can be used as a health food in the form of a tablet produced by a conventional tableting method, and it can be also used in foods, cosmetics and pharmaceuticals as an additive for imparting or supplementing the action of treating articular disorders.

EXAMPLE 2

Agent for Treating Articular Disorders

Three and half parts by weight of crystalline hydrous trehalose ("TREHA®", commercialized by Hayashibara Shoji Inc. Okayama, Japan), one part by weight of glucosamine ("NATURAL GLUCOSAMINE™", commercialized by Yaizu Suisankagaku Industry Co., Ltd., Shizuoka, Japan) and 0.5 part by weight of chondroitin 4-sulfate ("MUCOTEIN-DK™", commercialized by Yaizu Suisankagaku Industry Co., Ltd., Shizuoka, Japan) were mixed well to obtain the captioned product in the form of a powder.

Since the product remarkably exerts an action on articular disorders and has mild sweetness, it is useful to prevent or alleviate articular disorder such as arthritis and rheumatoid as a health food. The product can be used as a health food in the form of a tablet produced by a conventional tableting method, and it can be also used in foods, cosmetics and pharmaceuticals as an additive for imparting or supplementing the action for articular disorders.

EXAMPLE 3

Agent for Treating Articular Disorders

Four parts by weight of crystalline hydrous trehalose ("TREHA®", commercialized by Hayashibara Shoji Inc., Okayama, Japan), one part by weight of N-acetylglucosamine ("MARINE SWEET™", commercialized by Yaizu Suisankagaku Industry Co., Ltd., Shizuoka, Japan), 0.5 part by weight of chondroitin 4-sulfate ("MUCOTEIN-DK™", commercialized by Yaizu Suisankagaku Industry Co., Ltd.) and 0.1 part by weight of 2-O-alpha-D-glucopyranosyl L-ascorbic acid ("AA2G™", commercialized by Hayashibara Shoji Inc., Okayama, Japan) were mixed well to obtain the captioned product in a powder form.

Since the product remarkably exerts the action for treating articular disorders and has mild sweetness, it is useful to prevent or alleviate articular disorder such as arthritis and rheumatoid as a health food. The product can be used as a health food in the form of a tablet produced by a conventional tableting method, and it can be also used in foods, cosmetics and pharmaceuticals as an additive for imparting or supplementing the action for articular disorders.

EXAMPLE 4

Agent for Treating Articular Disorders

Five hundreds and fifty parts by weight of fine powdery crystalline hydrous aluminum silicate, 50 parts by weight of boric acid, 400 parts by weight of condense glycerin, four parts by weight of camphor, 0.5 part by weight of peppermint oil, 10 parts by weight of crystalline anhydrous maltitol ("MABIT®" (granule type), commercialized by Hayashibara Shoji Inc., Okayama, Japan) and 60 parts by weight of the agent for treating articular disorders of Example 1 were placed in a heat-resistant vessel and mixed well in a hot water bath to obtain the captioned product in a gel form.

Since the product can be used by attaching to the skin similarly as in conventional hot cataplasms, it can be used as a cataplasm to prevent or cure articulation disorders in various fields of pharmaceuticals, etc.

EXAMPLE 5

Soft Drink

One hundred and twenty grams of the agent for treating articular disorders of Example 2, 60 g of an isomerized sugar, 0.5 g of citric acid, and 0.5 g of L-ascorbic acid were dissolved in water and then filled up to 1 kg to produce a soft drink containing the agent for treating articular disorders. The product has a satisfactory taste and refreshment flavor due to a mild sweetness and adequate sourness.

Since the product has the action of treating articular disorders, it can be used as a health food or supplement to prevent or alleviate articular disorders.

EXAMPLE 6

Chewing Gum

Two parts by weight of unformed tablet composition, prepared by the method in Example 3 and contained one part by weight of N-acetylglucosamine ("MARINE SWEET™", commercialized by Yaizu Suisankagaku Industry Co., Ltd., Shizuoka, Japan), one part by weight of crystalline hydrous trehalose ("TREHA®", commercialized by Hayashibara Shoji Inc. Okayama, Japan), and a small amount of maltitol and sugarester were mixed with six parts by weight of glucose and two parts by weight of a gumbase, heated and dissolved until softened, further mixed with appropriate amount of a mint flavor, and kneaded with a roll in a conventional manner. The resultant was shaped into a chewing gum.

The product has a mild sweetness, refresh flavor, and satisfactory texture. Since the product has the action of treating articular disorders, it can be used as a health food or supplement for preventing or alleviating articular disorders.

EXAMPLE 7

Bath Salt

Sixty parts by weight of dried sodium sulfate, 30 parts by weight of sodium bicarbonate, five parts by weight of trehalose, two parts by weight of N-acetylglucosamine, one part by weight of chondroitin 4-sulfate, one part by weight of blended citrus flavor, and 0.5 part by weight of "Blue No. 2" were homogeneously mixed to obtain a bath salt.

When taking a bath, the product is used by dissolving about 20 g thereof in 100 L of hot bath-water. The product can moderately alleviate pain of articulation and stiff back due to its action for treating articular disorders.

INDUSTRIAL APPLICABILITY

As described above, the present invention was made based on a complete self-finding by the present inventors, which trehalose remarkably enhances the action of treating articular disorders by amino sugars. The agent for treating articular disorders of the present invention has more effect of completely recovering health from articular disorders than that attained by amino sugars alone. Also it can be used daily because the effective ingredients used in the agent are those found in nature. Therefore, the agent can prevent, alleviate or treat articular disorders such as arthritis, rheumatoids and arthropathy. The agent for treating articular disorders of the present invention can be advantageously used in foods, cosmetics and pharmaceuticals as a material because it has a satisfactory taste and has no problem in stimulating skins.

The present invention, having these outstanding effects and functions, is a significant invention that greatly contributes to this art.

The invention claimed is:

1. A composition for treating arthritis, comprising 0.1 to 40%(w/w) amino sugar and trehalose in one quarter to 20-folds amount of said amino sugar, both of which are on a dry solid basis.

2. The composition of claim 1, wherein said amino sugar is glucosamine, or mannosamine.

3. The composition of claim 1, which further contains a glycosaminoglycan.

4. The composition of claim 3, wherein said glycosaminoglycan is one or more members selected from the group consisting of chondroitin sulfate, chondroitin, dermatan sulfate, heparin, heparan sulfate, keratan sulfate, and hyaluronic acid.

5. The composition of claim 1, as part of a food, cosmetic, or pharmaceutical.

6. The composition of claim 1 in the form of a food product, further comprising at least one food component.

7. The composition of claim 1 in the form of a cosmetic composition, further comprising at least one cosmetically acceptable component suitable for topical application.

8. The composition of claim 1 in the form of a pharmaceutical composition, further comprising at least one pharmaceutically acceptable excipient.

9. The composition of claim 1, which further contains L-ascorbic acid or glycosyl L-ascorbic acid.

10. The composition of claim 9, wherein said glycosyl L-ascorbic acid is 2-O-α-D-glucopyranosyl L-ascorbic acid.

11. A method for treating arthritis, comprising administering to a subject an effective amount of the composition of claim 1.

12. The method of claim 11, wherein the subject is suffering from rheumatism.

13. The method of claim 11, wherein said composition is administered in an amount of at least 0.1 but less than 15 mg per kilogram of subject's body weight per day.

14. The method of claim 11, wherein said composition is administered in an amount of at least 0.1 but less than 5 mg per kilogram of the subject's body weight per day.

* * * * *